US006521815B1

United States Patent
Verma et al.

(10) Patent No.: US 6,521,815 B1
(45) Date of Patent: Feb. 18, 2003

(54) ANIMAL MODEL SYSTEM FOR SQUAMOUS CELL CARCINOMA

(75) Inventors: Ajit K. Verma, Madison, WI (US); Peter J. Reddig, Durham, NC (US); Aaron P. Jansen, New Market, MD (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/772,647

(22) Filed: Jan. 30, 2001

(51) Int. Cl.$^7$ .............................................. A01K 67/027
(52) U.S. Cl. ............................... 800/18; 800/3; 800/10; 800/25
(58) Field of Search .............................. 800/10, 18, 25, 800/3

(56) References Cited

PUBLICATIONS

Sigmund, C.D. (2000). Arterioscler Thromb Vasc Biol. 20:1425–1429.*
Wall, R.J. (1996). Theriogenology 45:57–68.*
Tseng, C–P. and Verma, A.K. 1996. Gene 169:287–288.*
Fujii, M. 1997. J. Stomatol. Soc. 64(1):52–66.*
Baxter, G. et al., "Constitutive presence of a catalytic fragment of protein kinase Cε in a small cell lung carcinoma cell line," J. Biol. Chem. 267: 1910–1917 (1992).
Cacae, A.M. et al., "The ε isoform of protein kinase C is an oncogene when overexpressed in rat fibroblasts," Oncogene 8: 2095–2104 (1993).
Denning, M.F. et al., "Specific protein kinase C isozymes mediate the induction of keratinocyte differentiation markers by calcium," Cell Growth Differ. 6: 149–157 (1995).
DiGiovanni, J., "Multistage carcinogenesis in mouse skin," Pharmacol. Ther. 54: 63–128 (1992).
Hennings, H. et al., "FVB/N mice: an inbred strain sensitive to the chemical induction of squamous cell carcinomas in the skin," Carcinogenesis 14: 2353–2358 (1993).
Mills, K.J. et al., "Alterations in protein kinase C isozymes α and β II in activated Ha–ras–containing papillomas in the absence of an increase in diacylglycerol," Carcinogenesis 13: 1113–1120 (1992).
Mischak, H. et al., "Overexpression of protein kinase C–δ and –ε in NIH 3T3 cells induces opposite effects on growth, morphology, anchorage dependence, and tumorigenicity," J. Biol. Chem. 268: 6090–6096 (1993).
Ono, Y. et al., "The structure, expression, and properties of additional members of the protein kinase C family," J. Biol. Chem. 263: 6927–6932 (1988).
Perletti, G.P. et al., "Overexpression of protein kinase C ε is oncogenic in rat colonic epithelial cells," Oncogene 12: 847–854 (1996).
Reddig, P.J. et al., "Transgenic mice overexpressing protein kinase Cε in their epidermis exhibit reduced papilloma burden but enhanced carcinoma formation after tumor production," Cancer Research 60: 595–602 (2000).
Reddig, P.J. et al., "Transgenic mice overexpressing protein kinase Cδ in the epidermis are resistant to skin tumor production by 12–O–Tetradecanoylphorbol–13–acetate," Cancer Research 59: 5710–5718 (1999).
Taketo, M. et al., "FVB/N mice sensitive to carcinogenesis," PNAS USA 88: 2065–2069 (1991).
Verma, A.K., "Protein kinase C and skin cancer prevention," In: H. Mukhtar (ed.), Skin Cancer: Mechanisms and Human Relevance, Ed. 1: 383–390 (1995).
Wang, X.J. et al., "Loss of mouse epidermal protein kinase C isozyme activities following treatment with phorbol ester and non–phorbol ester tumor promoters," Carcinogenesis 15: 2795–2803 (1994).

* cited by examiner

*Primary Examiner*—Remy Yucel
*Assistant Examiner*—Sita Pappu
(74) *Attorney, Agent, or Firm*—Quarles & Brady LLP

(57) ABSTRACT

Non-human mammalian animals having a higher epidermal expression level of protein kinase Cε than their wild-type counterparts are phenotypically distinguished from wild-type animals in that the animals induced to develop tumors in a chemical initiation/promotion protocol are suppressed for subsequent papilloma development but are susceptible to developing squamous cell carcinoma and metastatic squamous cell carcinoma. The animals are advantageously used in methods for screening putative agents for altering the susceptibility, development and progression of squamous cell carcinoma and metastatic squamous cell carcinoma and have further commercial value as tools for investigating the development of metastatic disease.

22 Claims, No Drawings

SEQUENCE LISTING

<160> NUMBER OF SEQ ID NOS: 6

<210> SEQ ID NO 1
<211> LENGTH: 2350
<212> TYPE: DNA
<213> ORGANISM: Homo sapiens

<400> SEQUENCE: 1

```
aagcttatat tccatgctag ggttctggtg ttggtgcgtg gggttggggt gggactgcag      60
aagtgccttt taagattatg tgattgactg atctgtcatt ggttccctgc catctttatc     120
ttttggattc ccctcggagg aggggaggaa ggagtttctt ttgggtttta ttgaatcaaa     180
tgaaagggaa agtagaggtg ttcctatgga ggggaggaag gagtttcttt tgggttttat     240
tgaatcaaat gaaagggaaa gtagaggtgt tcctatgtcc cgggctccgg agcttctatt     300
cctgggccct gcataagaag gagacatggt ggtggtggtg gtgggtgggg gtggtggggc     360
acagaggaag ccgatgctgg gctctgcacc ccattcccgc tcccagatcc ctctggatat     420
agcacccccct ccagtgagca cagcctcccc ttgccccaca gccaacagca acatgcctcc    480
caacaaagca tctgtccctc agccaaaacc cctgttgcct ctctctgggg aaattgtagg     540
gctgggccag ggtgggggga ccattctctg cagggagatt aggagtgtct gtcagggcg      600
ggtggagcgg ggtggggccc tggcttactc acatccttga gagtcctttg ctggcagatt     660
tggggagccc acagctcaga tgtctgtctc agcattgtct tccaagctcc taggccacag     720
tagtgggcg ctcccttctc tggcttcttc tttggtgaca gtcaaggtgg ggttgggggt      780
gacgaagggt cctgcttctc ttctaggagc agttgatccc aggaagagca ttggagcctc     840
cagcagggc tgttggggcc tgtctgagga gataggatgc gtcaggcagc cccagacacg      900
atcacattcc tctcaacatg cctgccgggg tctgtggagc cgaggggctg atgggagggt     960
ggggtggggg ccggaagggt ttgctttggg aggttgtctg ggagattgct gaagttttga   1020
tatacacacc tccaaagcag gaccaagtgg actcctagaa atgtcccctg acccttgggg   1080
cttcaggagt cagggaccct cgtgtccacc tcagccttgc ccttgcacag cccagctcca    1140
ctccagcctc tactcctccc cagaacatct cctgggccag ttccacaagg ggctcaaacg    1200
agggcacctg agctgcccac actagggatg ttctggggt ctgagaagat atctgggct     1260
ggaagaataa aaggcccccc taggcctgtt cctggatgca gctccagcca ctttgggct     1320
aagcctgggc aataacaatg ccaacgaggc ttcttgccat actcggttta caaacccctt    1380
tacatacatt gtcgcattgg attctcagag ctgactgcac taagcagaat agatggtatg   1440
actcccactt tgcagatgag aacactgagg ctcagagaag tgcgaagccc tgggtcacag   1500
aggcgtaaat gcagagccag gacccacctg aagacccacc tgactccagg atgtttcctg   1560
cctccatgag gccacctgcc ctatggtgtg gtggatgtga atcctcacc ataggaggga   1620
gattagggtc tgtgctcagg gctggggaga ggtgcctgga tttctctttg atggggatgt   1680
tggggtggga atcacgatac acctgatcag ctgggtgtat ttcagggatg gggcagactt   1740
```

-continued

```
ctcagcacag cacggcaggt caggcctggg agggccccca agacctcctt gtctctaata    1800
gagggtcatg gtgagggagg cctgtctgtg cccaaggtga ccttgccatg ccggtgcttt    1860
ccagccgggt atccatcccc tgcagcagca ggcttcctct acgtggatgt taaaggccca    1920
ttcagttcat ggagagctag caggaaacta ggtttaaggt gcagaggccc tgctctctgt    1980
caccctggct aagcccagtg cgtgggttcc tgagggctgg gactcccagg gtccgatggg    2040
aaagtgtagc ctgcaggccc acacctcccc ctgtgaatca cgcctggcgg acaagaaag    2100 cccaaaacac tccaaacaat gagtttccag taaaatatga cagacatgat gaggcggatg    2160
agaggaggga cctgcctggg agttggcgct agcctgtggg tgatgaaagc caaggggaat    2220
ggaaagtgcc agacccgccc cctacccatg agtataaagc actcgcatcc ctttgcaatt    2280
tacccgagca ccttctcttc actcagcctt ctgctcgctc gctcacctcc ctcctctgca    2340
ccatgactac                                                          2350
```

<210> SEQ ID NO 2
<211> LENGTH: 750
<212> TYPE: DNA
<213> ORGANISM: Mus musculus

<400> SEQUENCE: 2

```
tggcaagaag gtgctggctg ccttcagtga gggtctgagt cacctggaca acctcaaagg      60
cacctttgct aagctgagtg aactgcactg tgacaagctg cacgtggatc ctgagaactt     120
cagggtgagt ttggggaccc ttgattgttc tttcttttc gctattgtaa aattcatgtt     180
atatggaggg ggcaaagttt tcagggtgtt gtttagaatg ggaagatgtc ccttgtatca     240
ccatggaccc tcatgataat tttgtttctt tcactttcta ctctgttgac aaccattgtc     300
tcctcttatt ttctttttcat tttctgtaac ttttttcgtta aactttagct tgcatttgta     360 acgaatttt aaattcactt ttgtttattt gtcagattgt aagtactttc tctaatcact     420 ttttttcaa ggcaatcagg gtatattata ttgtacttca gcacagtttt agagaacaat     480
tgttataatt aaatgataag gtagaatatt tctgcatata aattctggct ggcgtggaaa     540
tattcttatt ggtagaaaca actacatcct ggtcatcatc ctgcctttct ctttatggtt     600
acaatgatat acactgtttg agatgaggat aaaatactct gagtccaaac cgggcccctc     660
tgctaaccat gttcatgcct tcttcttttt cctacagctc ctgggcaacg tgctggttat     720
tgtgctgtct catcattttg gcaaagaatt                                    750
```

<210> SEQ ID NO 3
<211> LENGTH: 2274
<212> TYPE: DNA
<213> ORGANISM: Artificial Sequence
<220> FEATURE:
<223> OTHER INFORMATION: Description of Artificial Sequence: T7 tag and
      mouse protein kinase C epsilon coding sequence
<221> NAME/KEY: CDS
<222> LOCATION: (61)..(2271)

<400> SEQUENCE: 3

```
atggctagca tgactggtgg acagcaaatg ggtcggatcc gaattcgagc tccgtcgacc      60 atg gta gtg ttc aat ggc ctt ctt aag atc aaa atc tgc gag gcg gtg     108
Met Val Val Phe Asn Gly Leu Leu Lys Ile Lys Ile Cys Glu Ala Val
1               5                   10                  15 agc ttg aag ccc aca gcc tgg tcg ctg cgc cat gcg gtg gga ccc cgg     156
Ser Leu Lys Pro Thr Ala Trp Ser Leu Arg His Ala Val Gly Pro Arg
            20                  25                  30
```

```
cca cag acg ttc ctt ttg gac ccc tac att gcc ctt aac gtg gac gac      204
Pro Gln Thr Phe Leu Leu Asp Pro Tyr Ile Ala Leu Asn Val Asp Asp
         35                  40                  45 tcg cgc atc ggc caa aca gcc acc aag caa aag acc aac agc ccg gcc      252
Ser Arg Ile Gly Gln Thr Ala Thr Lys Gln Lys Thr Asn Ser Pro Ala
 50                  55                  60 tgg cac gat gag ttc gtc acc gat gtg tgc aat ggg cgc aag atc gag      300
Trp His Asp Glu Phe Val Thr Asp Val Cys Asn Gly Arg Lys Ile Glu
 65                  70                  75                  80 ctg gct gtc ttt cac gac gct cct atc ggc tac gac gac ttc gtg gcc      348
Leu Ala Val Phe His Asp Ala Pro Ile Gly Tyr Asp Asp Phe Val Ala
                 85                  90                  95 aac tgc acc atc cag ttc gag gag ctg ctg cag aat ggg agc cgt cac      396
Asn Cys Thr Ile Gln Phe Glu Glu Leu Leu Gln Asn Gly Ser Arg His
             100                 105                 110 ttc gag gac tgg att gac ctg gag cca gaa gga aaa gtg tac gtg atc      444
Phe Glu Asp Trp Ile Asp Leu Glu Pro Glu Gly Lys Val Tyr Val Ile
         115                 120                 125 atc gat ctc tcg gga tca tcg ggt gaa gcc cct aaa gac aat gaa gaa      492
Ile Asp Leu Ser Gly Ser Ser Gly Glu Ala Pro Lys Asp Asn Glu Glu
130                 135                 140 cga gtg ttc agg gag cgt atg cgg cca agg aag cgg caa ggg gct gtc      540
Arg Val Phe Arg Glu Arg Met Arg Pro Arg Lys Arg Gln Gly Ala Val
145                 150                 155                 160 agg cgc agg gtc cac cag gtc aat ggc cac aag ttc atg gcc acc tac      588
Arg Arg Arg Val His Gln Val Asn Gly His Lys Phe Met Ala Thr Tyr
                 165                 170                 175 ttg cgg caa ccc acc tac tgc tcc cac tgc aga gat ttc atc tgg ggt      636
Leu Arg Gln Pro Thr Tyr Cys Ser His Cys Arg Asp Phe Ile Trp Gly
             180                 185                 190 gtc ata gga aaa cag gga tat caa tgt caa gtt tgc act tgc gtt gtc      684
Val Ile Gly Lys Gln Gly Tyr Gln Cys Gln Val Cys Thr Cys Val Val
         195                 200                 205 cac aag cga tgt cat gag ctc att att aca aag tgc gct ggg ctg aag      732
His Lys Arg Cys His Glu Leu Ile Ile Thr Lys Cys Ala Gly Leu Lys
         210                 215                 220 aaa cag gaa acc cct gac gag gtg ggc tcc caa cgg ttc agc gtc aac      780
Lys Gln Glu Thr Pro Asp Glu Val Gly Ser Gln Arg Phe Ser Val Asn
225                 230                 235                 240 atg ccc cac aag ttc ggg atc cac aac tac aag gtc ccc acg ttc tgt      828
Met Pro His Lys Phe Gly Ile His Asn Tyr Lys Val Pro Thr Phe Cys
                 245                 250                 255 gac cac tgt ggg tcc ctc ctc tgg ggc ctc ttg cgg cag ggc ttg cag      876
Asp His Cys Gly Ser Leu Leu Trp Gly Leu Leu Arg Gln Gly Leu Gln
             260                 265                 270 tgt aaa gtc tgc aaa atg aat gtt cac cgg cga tgt gag acc aac gtg      924
Cys Lys Val Cys Lys Met Asn Val His Arg Arg Cys Glu Thr Asn Val
         275                 280                 285 gct ccc aac tgt ggg gta gac gcc aga gga att gcc aaa gtg ctg gct      972
Ala Pro Asn Cys Gly Val Asp Ala Arg Gly Ile Ala Lys Val Leu Ala
         290                 295                 300 gac ctc ggt gtt act cca gac aaa atc acc aac agt ggc caa agg agg     1020
Asp Leu Gly Val Thr Pro Asp Lys Ile Thr Asn Ser Gly Gln Arg Arg
305                 310                 315                 320 aaa aag ctc gct gct ggt gct gag tcc cca cag ccg gct tct gga aac     1068
Lys Lys Leu Ala Ala Gly Ala Glu Ser Pro Gln Pro Ala Ser Gly Asn
                 325                 330                 335 tcc cca tct gaa gac gac cga tcc aag tca gcg ccc acc tcc cct tgt     1116
Ser Pro Ser Glu Asp Asp Arg Ser Lys Ser Ala Pro Thr Ser Pro Cys
```

-continued

|  |  |  |  |  |  |  |  |  |  |  |  |  |  |  |  |
|---|---|---|---|---|---|---|---|---|---|---|---|---|---|---|---|
|  |  | 340 |  |  |  | 345 |  |  |  | 350 |  |  |  |  |  |
| gac | cag | gaa | cta | aaa | gaa | ctt | gaa | aac | aac | atc | cgg | aag | gcc | ttg | tca | 1164 |
| Asp | Gln | Glu | Leu | Lys | Glu | Leu | Glu | Asn | Asn | Ile | Arg | Lys | Ala | Leu | Ser |  |
|  |  | 355 |  |  |  | 360 |  |  |  | 365 |  |  |  |  |  |
| ttt | gac | aac | cga | gga | gag | gag | cac | cga | gcg | tcg | tcg | gcc | acc | gat | ggc | 1212 |
| Phe | Asp | Asn | Arg | Gly | Glu | Glu | His | Arg | Ala | Ser | Ser | Ala | Thr | Asp | Gly |  |
|  | 370 |  |  |  |  | 375 |  |  |  | 380 |  |  |  |  |  |
| cag | ctg | gca | agc | ccc | gga | gag | aat | ggg | gaa | gtc | cgg | cca | ggc | cag | gcc | 1260 |
| Gln | Leu | Ala | Ser | Pro | Gly | Glu | Asn | Gly | Glu | Val | Arg | Pro | Gly | Gln | Ala |  |
| 385 |  |  |  |  | 390 |  |  |  |  | 395 |  |  |  |  | 400 |  |
| aag | cgc | ttg | ggg | ctg | gat | gag | ttc | aac | ttc | atc | aaa | gtg | ttg | ggc | aaa | 1308 |
| Lys | Arg | Leu | Gly | Leu | Asp | Glu | Phe | Asn | Phe | Ile | Lys | Val | Leu | Gly | Lys |  |
|  |  |  |  | 405 |  |  |  |  | 410 |  |  |  |  | 415 |  |  |
| ggc | agc | ttt | ggc | aag | gtc | atg | ttg | gcg | gaa | ctc | aaa | ggc | aaa | gat | gaa | 1356 |
| Gly | Ser | Phe | Gly | Lys | Val | Met | Leu | Ala | Glu | Leu | Lys | Gly | Lys | Asp | Glu |  |
|  |  |  | 420 |  |  |  |  | 425 |  |  |  |  | 430 |  |  |  |
| gtc | tac | gct | gtg | aag | gtc | ttg | aag | aag | gac | gtt | atc | cta | caa | gac | gat | 1404 |
| Val | Tyr | Ala | Val | Lys | Val | Leu | Lys | Lys | Asp | Val | Ile | Leu | Gln | Asp | Asp |  |
|  |  |  | 435 |  |  |  |  | 440 |  |  |  |  | 445 |  |  |  |
| gat | gtg | gac | tgc | aca | atg | aca | gag | aag | agg | att | ttg | gct | ctg | gct | cgg | 1452 |
| Asp | Val | Asp | Cys | Thr | Met | Thr | Glu | Lys | Arg | Ile | Leu | Ala | Leu | Ala | Arg |  |
|  | 450 |  |  |  |  | 455 |  |  |  |  | 460 |  |  |  |  |  |
| aaa | cac | cct | tat | cta | acc | caa | ctc | tat | tgc | tgc | ttc | cag | acc | aag | gac | 1500 |
| Lys | His | Pro | Tyr | Leu | Thr | Gln | Leu | Tyr | Cys | Cys | Phe | Gln | Thr | Lys | Asp |  |
| 465 |  |  |  |  | 470 |  |  |  |  | 475 |  |  |  |  | 480 |  |
| cgc | ctc | ttc | ttc | gtc | atg | gaa | tat | gta | aat | ggt | gga | gac | ctc | atg | ttc | 1548 |
| Arg | Leu | Phe | Phe | Val | Met | Glu | Tyr | Val | Asn | Gly | Gly | Asp | Leu | Met | Phe |  |
|  |  |  |  |  | 485 |  |  |  |  | 490 |  |  |  |  | 495 |  |
| cag | att | cag | cgg | tcc | cga | aaa | ttt | gat | gag | cct | cgt | tct | cgg | ttc | tat | 1596 |
| Gln | Ile | Gln | Arg | Ser | Arg | Lys | Phe | Asp | Glu | Pro | Arg | Ser | Arg | Phe | Tyr |  |
|  |  |  | 500 |  |  |  |  | 505 |  |  |  |  | 510 |  |  |  |
| gcc | gca | gag | gtc | aca | tcg | gcc | ctc | atg | ttt | ctc | cac | cag | cat | gga | gtg | 1644 |
| Ala | Ala | Glu | Val | Thr | Ser | Ala | Leu | Met | Phe | Leu | His | Gln | His | Gly | Val |  |
|  |  |  | 515 |  |  |  |  | 520 |  |  |  |  | 525 |  |  |  |
| atc | tac | agg | gat | ttg | aaa | ctg | gac | aac | atc | ctt | cta | gat | gca | gaa | ggc | 1692 |
| Ile | Tyr | Arg | Asp | Leu | Lys | Leu | Asp | Asn | Ile | Leu | Leu | Asp | Ala | Glu | Gly |  |
|  | 530 |  |  |  |  | 535 |  |  |  |  | 540 |  |  |  |  |  |
| cac | tgc | aag | ctg | gct | gac | ttt | ggg | atg | tgc | aag | gaa | ggg | att | atg | aat | 1740 |
| His | Cys | Lys | Leu | Ala | Asp | Phe | Gly | Met | Cys | Lys | Glu | Gly | Ile | Met | Asn |  |
| 545 |  |  |  |  | 550 |  |  |  |  | 555 |  |  |  |  | 560 |  |
| ggt | gtg | aca | act | acc | acc | ttc | tgt | ggg | act | cct | gac | tac | ata | gct | cca | 1788 |
| Gly | Val | Thr | Thr | Thr | Thr | Phe | Cys | Gly | Thr | Pro | Asp | Tyr | Ile | Ala | Pro |  |
|  |  |  |  | 565 |  |  |  |  | 570 |  |  |  |  | 575 |  |  |
| gag | atc | cta | cag | gag | ttg | gag | tac | ggc | ccc | tca | gtg | gac | tgg | tgg | gcc | 1836 |
| Glu | Ile | Leu | Gln | Glu | Leu | Glu | Tyr | Gly | Pro | Ser | Val | Asp | Trp | Trp | Ala |  |
|  |  |  | 580 |  |  |  |  | 585 |  |  |  |  | 590 |  |  |  |
| ctg | gga | gtg | ctg | atg | tac | gag | atg | atg | gct | ggg | cag | ccc | ccc | ttt | gaa | 1884 |
| Leu | Gly | Val | Leu | Met | Tyr | Glu | Met | Met | Ala | Gly | Gln | Pro | Pro | Phe | Glu |  |
|  |  |  | 595 |  |  |  |  | 600 |  |  |  |  | 605 |  |  |  |
| gct | gac | aac | gag | gac | gac | ttg | ttc | gaa | tcc | atc | ctt | cat | gat | gat | gtt | 1932 |
| Ala | Asp | Asn | Glu | Asp | Asp | Leu | Phe | Glu | Ser | Ile | Leu | His | Asp | Asp | Val |  |
|  | 610 |  |  |  |  | 615 |  |  |  |  | 620 |  |  |  |  |  |
| ctc | tat | cct | gtc | tgg | ctc | agc | aag | gaa | gct | gtc | agc | atc | ctg | aaa | gct | 1980 |
| Leu | Tyr | Pro | Val | Trp | Leu | Ser | Lys | Glu | Ala | Val | Ser | Ile | Leu | Lys | Ala |  |
| 625 |  |  |  |  | 630 |  |  |  |  | 635 |  |  |  |  | 640 |  |
| ttc | atg | acc | aag | aac | ccg | cac | aag | cgc | ctg | ggc | tgt | gtg | gca | gcg | cag | 2028 |
| Phe | Met | Thr | Lys | Asn | Pro | His | Lys | Arg | Leu | Gly | Cys | Val | Ala | Ala | Gln |  |
|  |  |  |  | 645 |  |  |  |  | 650 |  |  |  |  | 655 |  |  |
| aac | ggg | gag | gac | gcc | atc | aag | caa | cat | cca | ttc | ttc | aag | gag | att | gac | 2076 |

```
Asn Gly Glu Asp Ala Ile Lys Gln His Pro Phe Phe Lys Glu Ile Asp
            660                 665                 670 tgg gta ctg ctg gag cag aag aaa atc aag ccc ccc ttc aag ccg aga      2124
Trp Val Leu Leu Glu Gln Lys Lys Ile Lys Pro Pro Phe Lys Pro Arg
        675                 680                 685 att aaa acc aaa aga gat gtc aat aac ttt gac caa gac ttt acg cgg      2172
Ile Lys Thr Lys Arg Asp Val Asn Asn Phe Asp Gln Asp Phe Thr Arg
690                 695                 700 gaa gag cca ata ctt aca ctt gtg gat gaa gca atc att aag cag atc      2220
Glu Glu Pro Ile Leu Thr Leu Val Asp Glu Ala Ile Ile Lys Gln Ile
705                 710                 715                 720 aac cag gaa gaa tty aaa ggc ttc tcc tac ttt ggt gaa gac ctg atg      2268
Asn Gln Glu Glu Phe Lys Gly Phe Ser Tyr Phe Gly Glu Asp Leu Met
                725                 730                 735 ccc tga                                                               2274
Pro

<210> SEQ ID NO 4
<211> LENGTH: 737
<212> TYPE: PRT
<213> ORGANISM: Artificial Sequence
<220> FEATURE:
<223> OTHER INFORMATION: Description of Artificial Sequence: T7 tag and
<223> OTHER INFORMATION: mouse protein kinase C epsilon coding sequence

<400> SEQUENCE: 4

Met Val Val Phe Asn Gly Leu Leu Lys Ile Lys Ile Cys Glu Ala Val
 1               5                  10                  15

Ser Leu Lys Pro Thr Ala Trp Ser Leu Arg His Ala Val Gly Pro Arg
                20                  25                  30

Pro Gln Thr Phe Leu Leu Asp Pro Tyr Ile Ala Leu Asn Val Asp Asp
            35                  40                  45

Ser Arg Ile Gly Gln Thr Ala Thr Lys Gln Lys Thr Asn Ser Pro Ala
    50                  55                  60

Trp His Asp Glu Phe Val Thr Asp Val Cys Asn Gly Arg Lys Ile Glu
65                  70                  75                  80

Leu Ala Val Phe His Asp Ala Pro Ile Gly Tyr Asp Asp Phe Val Ala
                85                  90                  95

Asn Cys Thr Ile Gln Phe Glu Glu Leu Leu Gln Asn Gly Ser Arg His
            100                 105                 110

Phe Glu Asp Trp Ile Asp Leu Glu Pro Glu Gly Lys Val Tyr Val Ile
        115                 120                 125

Ile Asp Leu Ser Gly Ser Ser Gly Glu Ala Pro Lys Asp Asn Glu Glu
    130                 135                 140

Arg Val Phe Arg Glu Arg Met Arg Pro Arg Lys Arg Gln Gly Ala Val
145                 150                 155                 160

Arg Arg Arg Val His Gln Val Asn Gly His Lys Phe Met Ala Thr Tyr
                165                 170                 175

Leu Arg Gln Pro Thr Tyr Cys Ser His Cys Arg Asp Phe Ile Trp Gly
            180                 185                 190

Val Ile Gly Lys Gln Gly Tyr Gln Cys Gln Val Cys Thr Cys Val Val
        195                 200                 205

His Lys Arg Cys His Glu Leu Ile Ile Thr Lys Cys Ala Gly Leu Lys
    210                 215                 220

Lys Gln Glu Thr Pro Asp Glu Val Gly Ser Gln Arg Phe Ser Val Asn
225                 230                 235                 240

Met Pro His Lys Phe Gly Ile His Asn Tyr Lys Val Pro Thr Phe Cys
```

-continued

```
                245                 250                 255
Asp His Cys Gly Ser Leu Leu Trp Gly Leu Leu Arg Gln Gly Leu Gln
            260                 265                 270

Cys Lys Val Cys Lys Met Asn Val His Arg Arg Cys Glu Thr Asn Val
            275                 280                 285

Ala Pro Asn Cys Gly Val Asp Ala Arg Gly Ile Ala Lys Val Leu Ala
            290                 295                 300

Asp Leu Gly Val Thr Pro Asp Lys Ile Thr Asn Ser Gly Gln Arg Arg
305                 310                 315                 320

Lys Lys Leu Ala Ala Gly Ala Glu Ser Pro Gln Pro Ala Ser Gly Asn
                325                 330                 335

Ser Pro Ser Glu Asp Asp Arg Ser Lys Ser Ala Pro Thr Ser Pro Cys
            340                 345                 350

Asp Gln Glu Leu Lys Glu Leu Glu Asn Asn Ile Arg Lys Ala Leu Ser
            355                 360                 365

Phe Asp Asn Arg Gly Glu Glu His Arg Ala Ser Ser Ala Thr Asp Gly
            370                 375                 380

Gln Leu Ala Ser Pro Gly Glu Asn Gly Glu Val Arg Pro Gly Gln Ala
385                 390                 395                 400

Lys Arg Leu Gly Leu Asp Glu Phe Asn Phe Ile Lys Val Leu Gly Lys
                405                 410                 415

Gly Ser Phe Gly Lys Val Met Leu Ala Glu Leu Lys Gly Lys Asp Glu
            420                 425                 430

Val Tyr Ala Val Lys Val Leu Lys Lys Asp Val Ile Leu Gln Asp Asp
            435                 440                 445

Asp Val Asp Cys Thr Met Thr Glu Lys Arg Ile Leu Ala Leu Ala Arg
450                 455                 460

Lys His Pro Tyr Leu Thr Gln Leu Tyr Cys Cys Phe Gln Thr Lys Asp
465                 470                 475                 480

Arg Leu Phe Phe Val Met Glu Tyr Val Asn Gly Gly Asp Leu Met Phe
                485                 490                 495

Gln Ile Gln Arg Ser Arg Lys Phe Asp Glu Pro Arg Ser Arg Phe Tyr
            500                 505                 510

Ala Ala Glu Val Thr Ser Ala Leu Met Phe Leu His Gln His Gly Val
            515                 520                 525

Ile Tyr Arg Asp Leu Lys Leu Asp Asn Ile Leu Leu Asp Ala Glu Gly
            530                 535                 540

His Cys Lys Leu Ala Asp Phe Gly Met Cys Lys Glu Gly Ile Met Asn
545                 550                 555                 560

Gly Val Thr Thr Thr Thr Phe Cys Gly Thr Pro Asp Tyr Ile Ala Pro
                565                 570                 575

Glu Ile Leu Gln Glu Leu Glu Tyr Gly Pro Ser Val Asp Trp Trp Ala
            580                 585                 590

Leu Gly Val Leu Met Tyr Glu Met Met Ala Gly Gln Pro Pro Phe Glu
            595                 600                 605

Ala Asp Asn Glu Asp Asp Leu Phe Glu Ser Ile Leu His Asp Asp Val
            610                 615                 620

Leu Tyr Pro Val Trp Leu Ser Lys Glu Ala Val Ser Ile Leu Lys Ala
625                 630                 635                 640

Phe Met Thr Lys Asn Pro His Lys Arg Leu Gly Cys Val Ala Ala Gln
                645                 650                 655

Asn Gly Glu Asp Ala Ile Lys Gln His Pro Phe Phe Lys Glu Ile Asp
            660                 665                 670
```

```
Trp Val Leu Leu Glu Gln Lys Lys Ile Lys Pro Pro Phe Lys Pro Arg
        675                 680                 685

Ile Lys Thr Lys Arg Asp Val Asn Asn Phe Asp Gln Asp Phe Thr Arg
    690                 695                 700

Glu Glu Pro Ile Leu Thr Leu Val Asp Glu Ala Ile Ile Lys Gln Ile
705                 710                 715                 720

Asn Gln Glu Glu Phe Lys Gly Phe Ser Tyr Phe Gly Glu Asp Leu Met
                725                 730                 735

Pro

<210> SEQ ID NO 5
<211> LENGTH: 598
<212> TYPE: DNA
<213> ORGANISM: Homo sapiens

<400> SEQUENCE: 5
tcaggcctag gaggccccccc gtgtggacac agatcccact ggaagatccc ctctcctgcc      60
caagcacttc acagctggac cctgcttcac cctcaccccc tcctggcaat caatacagct     120
tcattatctg agttgcataa ttctcgcctc tctctggtca ttgttaggag tgggggtggg     180
gagaaagtgg gagagcatct ctttggagct tgtcatgcac ctggctatgg ccctgggac      240 tgggagaaaa gtcctggggg tgggttgggc tcaggtccca ggatatcttt cgccatctca     300
gaagacacag atagatgtgt gtaccaggtc atatgtggtg tctcctaggg tacggaggga     360
tattcattca tttactcact cattttcatg tgtgtccatt cattcaccag atattgagtg     420
cctctatgtc aggcactatg ttaggttaag gattcctgat gtttttgtgt atcagggatt     480
ccttggagaa tattgaaagc tatagatctt tccttctgcc ccctaccttc aaataagcat     540
acatacattt gcatacatgt catggggttc atgggtctcc tagagctcct taccggag      598

<210> SEQ ID NO 6
<211> LENGTH: 9
<212> TYPE: PRT
<213> ORGANISM: Mus musculus

<400> SEQUENCE: 6

Glu Arg Lys Arg Thr Leu Arg Arg Leu
  1               5
```

ANIMAL MODEL SYSTEM FOR SQUAMOUS CELL CARCINOMA

CROSS-REFERENCE TO RELATED APPLICATIONS

Not applicable.

STATEMENT REGARDING FEDERALLY SPONSORED RESEARCH OR DEVELOPMENT

This invention was made with United States government support awarded by the following agencies:

NIH CA35368.

The United States has certain rights in this invention.

BACKGROUND OF THE INVENTION

A majority of human cancers originate from epithelial tissue. A common cancer of epithelial origin is nonmelanoma skin cancer (NMSC), including basal cell carcinoma (BCC) and squamous cell carcinoma (SCC), with more than 700,000 new cases diagnosed each year in the United States. Similar cancers are also seen in non-human animals such as domesticated animals and pets, including cats and dogs. BCC is rarely life-threatening because it is slow growing and is mostly localized. Unlike BCC, SCC metastasizes at a rate of 2% to 6% over several years after initial diagnosis. A highly malignant form invades and destroys tissue, and then metastasizes, initially to a regional lymph node before more distant organs such as the lung or brain are affected. SCC is commonly encountered in a number of epithelial tissues, including the oral cavity, esophagus, larynx, bronchi, intestines, colon, genital tract, and skin. Early detection using reliable biomarkers is desired, as are rationally designed drugs for effectively preventing and treating aggressive, metastatic SCC.

As such, there is a need for a good animal model system for studying how metastatic squamous cell carcinoma develops, progresses and can be treated. To date, no such model exists. Classically, tumor cells are injected into the tail vein of either immunocompromised or syngeneic mice. While this assay can suitably model the later metastatic stages, it does not model the early genesis, invasion and angiogenic stages of malignant progression, especially as it relates to complex interactions between tumor and host, especially at the tissue site where the carcinoma originated. Moreover, the role of the immune system in metastatic progression cannot be analyzed when immunocompromised mice are used.

Murine skin model systems are still essential contributors to our understanding of the multi-step nature of chemically-induced carcinogenesis. In the multistage mouse skin carcinogenesis model, biochemical events unique to initiation, promotion, or progression can be studied and related to cancer formation. In that model, the NMSC that is most often induced is squamous cell carcinoma. Although squamous cell carcinoma of mouse skin invades the dermal region, the incidence of malignant metastatic conversion is rare and requires a long latency period of approximately a year.

Several protocols are used to develop mouse skin tumors in laboratory animals. In a common initiation-promotion protocol, mouse skin is treated with an initiating agent (7,12-dimethylbenz[a]anthracene; DMBA) and then with a potent tumor promoter (12-O-tetradecanoylphorbol-13-acetate; TPA). In this protocol, mice develop mostly benign papillomas, more than 90% of which regress after TPA treatment is stopped. Only a small percentage of papillomas progress to invasive, but non-metastatic, SCC. The initiation-promotion protocol has been further modified to enhance the conversion of skin papillomas to carcinomas, yet metastatic potential is not increased.

A major intracellular receptor for TPA is the ubiquitous enzyme protein kinase C (PKC), an important signal transduction pathway component for controlling cell proliferation and tumorigenesis. It has been suggested that PKC activation may play a role in promoting mouse skin tumor formation. However, several groups have demonstrated that repeated applications of TPA depress PKC activity and protein levels. These results indicate that both loss of PKC activity and degradation of PKC could be important for mouse skin tumor promotion by TPA.

On the basis of the structural similarities and cofactor requirements, the eleven known PKC isoforms are grouped into three subfamilies: (1) the conventional PKCs ($\alpha$, $\beta$I, $\beta$II, and $\gamma$), which depend upon $Ca^{2+}$, phosphatidylserine (PS), and diacylglycerol (DAG) or TPA; (2) the nPKCs ($\epsilon$, $\delta$, $\eta$, and $\theta$), which require only PS and DAG/TPA; and (3) the atypical PKCs ($\iota/\lambda$ and $\xi$), which retain PS dependence but have no requirement for $Ca^{2+}$ or DAG/TPA for activation. PKC$\mu$, which is usually classified as a nPKC, is not easily grouped with any of the other isoforms.

The roles of PKC$\alpha$ and PKC$_\delta$ isoforms in the mouse skin tumor initiation/promotion protocol were assessed in FVB/N transgenic mice expressing an T7-epitope-tagged PKC$\alpha$ (T7-PKC$\alpha$) or PKC$\delta$ (T7-PKC$\delta$) under the control of the human keratinocyte-specific K14 promoter/enhancer. Transgenic expression of T7-PKC$\alpha$ did not affect tumor promotion susceptibility. Transgenic expression of T7-PKC$\delta$ in the epidermis (~8-fold increase) suppressed the formation of both skin papillomas and carcinomas by 70%.

PKC$\epsilon$ may play an important role in cellular growth regulation. TPA binds to and activates PKC$\epsilon$. Activated PKC$\epsilon$ may be important for the survival of small cell lung carcinoma cell lines in which the catalytic fragment of PKC$\epsilon$ is constitutively expressed. Overexpression of PKC$\epsilon$ in Rat-6 or NIH-3T3 fibroblasts increases growth rate, anchorage independence, and tumor formation in nude mice. PKC$\epsilon$ overexpression also transforms non-tumorigenic rat colonic epithelial cells and suppresses apoptosis of interleukin-3 dependent human myeloid cells induced by removal of interleukin-3.

The role of PKC$\epsilon$ in mouse skin tumor promotion and epidermal cell growth and differentiation remains unclear. Treatment of the mouse skin with TPA leads to a general reduction in PKC activity that persists for at least 4 days. Acute TPA treatment decreases PKC$\beta$ and $\eta$ protein levels, but has little or no effect on the levels of PKC$\alpha$, $\delta$, or $\epsilon$. PKC$\alpha$, $\beta$, and $\delta$ activity levels were reduced after acute or repeated TPA treatments, but PKC$\epsilon$ activity was not examined. DMBA/TPA-induced papillomas exhibit decreased cytosolic levels of PKC$\alpha$ and $\beta$II protein, but insignificant alterations in the levels of PKC$\delta$, $\epsilon$, or $\xi$ protein. When cultured mouse skin keratinocytes are induced to differentiate by increasing $Ca^{2+}$, PKC$\epsilon$, $\delta$, and a translocate to the membrane fraction, suggesting a role for activation of these isoforms in keratinocyte differentiation.

BRIEF SUMMARY OF THE INVENTION

The present invention is summarized in that an FVB/N mouse that expresses more PKC$\epsilon$ in its epidermis than in the epidermis of a wild-type FVB/N mouse is a useful model for development and treatment of skin cancer, particularly squamous cell carcinoma, in human and non-human mammalian animals. In a preferred embodiment, the mouse expresses at least about 5-fold more epidermal PKCε than wild-type FVB/N mice, with more preferred embodiments having still higher levels of epidermal PKCε.

The present invention is also summarized in that an FVB/N mouse that expresses PKCε in its epidermis at a level higher than a wild-type FVB/N mouse, where the level is sufficiently high to induce metastatic growth, is a useful model for development and treatment of metastatic skin cancer, particularly for metastatic squamous cell carcinoma, in humans. Notably the mice constitute a model system for developing and treating highly malignant metastatic squamous cell carcinoma. A level sufficiently high is more than 5-fold higher than in wild-type FVB/N mice, and is preferably at least about 12-fold higher, and still more preferably at least about 15-fold higher, and most preferably at least about 18-fold higher.

The present invention is also summarized in that a method for inducing squamous cell carcinomas in the aforementioned mice includes the steps of treating the mouse with a skin tumor initiating chemical agent, then treating the mouse repeatedly with an skin tumor promotion chemical agent for a time sufficient to induce squamous cell carcinomas and then screening the treated mice to identify those mice in which squamous cell carcinoma is induced. In a related embodiment, the skin tumor initiating agent can be DMBA and the skin tumor promotion agent can be TPA. After treatment according to the method, the mice of the invention are characteristically suppressed for papilloma formation, even though squamous cell carcinoma is observed at an enhanced rate. The mice having squamous cell carcinoma disease produced in the inducing method are also an useful animal model for development and treatment of squamous cell carcinoma induced by non-chemical agents such as ultraviolet radiation.

In a related aspect, the present invention is further summarized in that a method for inducing squamous cell carcinomas in FVB/N mice that express PKCε in its epidermis at the aforementioned level sufficiently high to induce metastatic growth consists essentially of the step of treating the mice with an initiating agent without further treatment with a promoting agent.

In a related embodiment, the present invention is summarized in that a method for inducing metastatic moderately differentiated squamous cell (MDSC) carcinomas in an FVB/N mouse that expresses at least about 12-fold more PKCε in its epidermis than a wild-type FVB/N mouse includes the steps of treating the mouse with a skin tumor initiating agent and then treating the mouse repeatedly with an skin tumor promotion agent for a time sufficient to allow metastatic involvement, typically, but not exclusively, of the lymph nodes. The metastatic MDSC thus induced appear to originate from the hair follicle within squamous cells located near the sebaceous gland ("bulge region") that are postulated to be progenitor or stem cells for the hair follicle and epidermis. The metastatic MDSC are pathologically distinguishable by histogenesis from the well differentiated squamous cell carcinomas (WDSC) observed in FVB/N mice having a wild-type PKCε level that appear to originate instead from the interfollicular epidermis and which invade the dermis and subcutaneous tissues, but remain localized.

In a related aspect, the invention is summarized in that a method for evaluating the effectiveness of putative agents against squamous cell carcinoma in a mammal includes the steps of administering various doses of at least one putative agent over an appropriate range to mice of the invention that have squamous cell carcinoma, evaluating the effect of the agent on development or progression of the squamous cell carcinoma, and selecting at least one agent having anti-squamous cell carcinoma activity.

The invention is still further summarized in that a method for evaluating the effectiveness of putative agents against metastatic squamous cell carcinoma in a mammal includes the steps of administering at least one putative agent in varying amounts to mice of the invention having metastatic squamous cell carcinoma, evaluating the effect of the agent on development or progression of the metastatic squamous cell carcinoma, and selecting at least one agent having anti-metastatic squamous cell carcinoma activity.

The present invention is also summarized in that a mouse that expresses at leas about 5-fold more PKCε in its epidermis than a wild-type FVB/N mouse can be made by increasing the rate at which a PKCε-encoding polynucleotide is transcribed, by decreasing the rate at which a transcript of the PKCε-encoding polynucleotide is degraded, or by increasing the stability of the transcript or of a resulting PKCε protein in epidermal cells.

In a related aspect, the present invention is summarized in that a method of making a mouse that expresses at least about 5-fold more PKCε in its epidermis than a wild-type FVB/N mouse includes the steps of introducing into a one cell fertilized FVB/N embryo a chimeric transgene that comprises a polynucleotide that encodes PKCε under the transcriptional control of an upstream promoter active in keratinocytes and a downstream polyA addition sequence, implanting the embryo in a carrying animal, screening progeny of a cross between offspring of the carrier animal and FVB/N mice for expression of the transgene for PKCε expression level, and selecting transgenic offspring having increased PKCε expression.

The present invention is yet further summarized in that a transgene for use in the method of making a mouse that expresses at least about 5-fold more PKCε in its epidermis than a wild-type FVB/N mouse comprises a polynucleotide that encodes PKCε under the transcriptional control of an upstream promoter active in keratinocytes and a downstream polyA addition sequence, and optionally includes a polynucleotide that encodes a peptide tag adjacent to the polynucleotide that encodes PKCε and further optionally includes one or more other transcription enhancing elements.

It is an object of the invention to provide a non-human animal model system for cutaneous squamous cell carcinoma and metastatic squamous cell carcinoma in other human and non-human mammalian animals.

It is another object of the invention to provide an animal model system where the non-human animal develops an aggressively malignant and metastatic disease.

It is a feature of the present invention that carcinomas induced in the mice of the invention in a two-stage tumor initiation/promotion method suppress the formation of skin papillomas and enhance the formation of moderately differentiated squamous cell carcinomas.

It is another feature of the present invention that when the level of PKCε is sufficiently high in mice of the invention, moderately differentiated squamous cell carcinomas of the animals rapidly metastasize to regional lymph nodes, thereby mirroring cutaneous metastatic squamous cell carcinoma disease in humans and other non-human mammalian animals.

It is an advantage of the present invention over existing murine model systems in that the invention permits study of metastatic development in a timely manner.

It is yet another advantage of the present invention that the carcinogen is administered topically.

It is yet another advantage of the present invention that the carcinomas appear rapidly, within 15 to 25 weeks, thus facilitating its use in screening for agents that can prevent induction of metastatic SCC and as a model for investigating the genesis and progression of SCC, and the molecular events associated with progression and metastasis.

Other objects, advantages and features of the invention will become apparent upon consideration of the following detailed description.

BRIEF DESCRIPTION OF THE SEVERAL VIEWS OF THE DRAWINGS

Not applicable.

DETAILED DESCRIPTION OF THE INVENTION

The present invention relates to a murine model system for development and progression of squamous cell carcinomas, and more particularly a model system for development and progression of metastatic carcinomas and methods for making and using mice for evaluating agents for modulating development and progression of metastatic carcinomas, as well as the mice per se. Certain aspects of this invention are described in Reddig, P. J. et al., "Transgenic Mice Overexpressing Protein Kinase Cε in Their Epidermis Exhibit Reduced Papilloma Burden but Enhanced Carcinoma Formation after Tumor Promotion," *Cancer Research* 60:595 (2000) incorporated herein by reference as if set forth in its entirety.

Mice within the scope of the invention are characterized as FVB/N mice that express PKCε at or above about five times the level seen in wild-type FVB/N mice. The effects that result from elevated epidermal PKCε levels vary as the epidermal level increases. Overexpression of PKCε in the untreated mouse epidermis leads to phenotypic abnormalities (such as inflamation, hyperkeratosis, hyperplasia, cellular hypertrophy, and ulceration), especially of the skin surrounding the tail base of older mice (approximately 7–8 months of age).

Of particular note in the disclosed system is the different character of the tumors induced in mice of the invention after a tumor initiation/promotion regimen. The mice of the invention are suppressed for papilloma formation and instead develop moderately differentiated squamous cell carcinomas (MDSC) without requiring papillomas as a precursor. The MDSC appear to originate from the hair follicle within squamous cells located near the sebaceous gland ("bulge region"). The bulge cells are thought to be progenitor or stem cells for the hair follicle and epidermis. Interestingly, after treatment certain mice of the invention also develop papilloma-independent squamous cell carcinoma that metastasizes rapidly to the lymph nodes when the activity level of PKCε in the epidermis is particularly high, say, at least about 12-fold higher than the wild-type level, or more preferably greater than 15 fold higher, most preferably about 18 fold higher.

In contrast, wild-type FVB/N mice treated in the same regimen typically first develop papillomas and then well differentiated squamous cell carcinomas (WDSC) that invade the dermis and subcutaneous tissues but remain localized. The WDSC largely appear to originate from the interfollicular epidermis.

The mice and methods of the invention provide a unique opportunity to study the origin and events associated with malignant progression (and interruption thereof) and have direct commercial value to the biotechnology community as a result. Separately, the mice and methods provide a resource with which to evaluate the role of PKCε in tumorigenesis. The difference in metastatic potential and the different origin of malignancy support the conclusion that T7-PKCε papilloma-independent carcinomas are pathologically distinct from the mouse carcinomas seen in treated wild-type FVB/N mice.

Mice having elevated epidermal PKCε activity levels in accordance with the invention can be produced by increasing the rate at which a PKCε-encoding polynucleotide sequence is transcribed, by decreasing the rate at which the transcript is degraded, or by increasing the stability of the transcript or of the resulting PKCε protein in epidermal cells. One suitable and convenient method for increasing the PKCε level in epidermal cells is to provide in the cells a transgene that comprises a known PKCε coding sequence flanked upstream by a promoter effective in the target skin cells and downstream by a suitable polyA sequence, preferably from the same source as the promoter sequence. Other elements that can be provided on the transgene include transcription enhancing sequences, such as a β-globin intron, or sequences that can aid in detecting the encoded PKCε protein, such as a T7 tag that can be readily detected using a commercially available horseradish peroxidase-conjugated anti-T7-tag antibody(Novagen, Inc., Madison, Wis.). Preferably, the additional sequences should not negatively affect the expression or activity of the PKCε protein.

Nucleotide sequences for the components of a suitable transgene are attached in the Sequence Listing. A K14 promoter/enhancer sequence from humans is attached as SEQ ID NO:1. A suitable β-globin intron is attached as SEQ ID NO:2. A PKCε encoding polynucleotide sequence from mice is attached as SEQ ID NO:3. At the 5' end of SEQ ID NO:3 is a T7 tag sequence. SEQ ID NO:4 depicts the encoded PKCε polypeptide sequence. SEQ ID NO:5 is a K14 poly A addition sequence from humans. The skilled artisan will appreciate that the functions of the disclosed sequences are not adversely affected by certain mutations in the aforementioned polynucleotide and amino acid sequences, including insertions, deletions or substitutions, including but not limited to changes that result in conservative changes to any resulting amino acid sequence. Moreover, some changes in either the PKCε coding sequence or a regulatory sequence can increase the PKCε activity in the epidermis and such changes are specifically contemplated to be within the scope of the invention.

The transgene can be provided to epidermal cells or to cells that mature into epidermal cells, such as keratinocytes or keratinocyte precursor cells. Most preferably, the transgene is inserted into an early stage fertilized embryo in a method for making transgenic mice. The embryo is allowed to mature in a manner known to the art. Introduction of the chimeric gene into the fertilized egg of the mammal is accomplished by any number of standard techniques in transgenic technology (Hogan et al., 1986, Manipulating the Mouse Embryo: A Laboratory Manual, Cold Spring Harbor, N.Y.). Most commonly, the chimeric gene is introduced into the embryo by way of microinjection. The PKCε-encoding polynucleotide sequence under the control of the strong heterologous promoter can conveniently be introduced into the recipient mouse strain by microinjection of a chimeric expression cassette (or "transgene") into pronuclei, preferably male pronuclei, of 1-cell fertilized mouse embryos using known transgenic method as described below in connection with the working embodiment of the invention. Other methods, including classical breeding methods, can also be used to produce animals expressing elevated levels of PKCε in the skin of the animal.

It is important to perform the transgenic technique with a recipient mouse strain that is both susceptible to tumor formation and to transgenic uptake of exogenous DNA. Moreover, the mouse strain should be inbred to eliminate undesired and uncontrollable effects that can be introduced by heterozygosity. Mice suitable for use in the methods of the invention, including the method for producing transgenic mice, are FVB/N inbred mice (commercially available from Taconic Farms, Inc.) and closely related strains and derivatives thereof, although other mouse strains may also be suitable. The FVB/N inbred mouse strain produces eggs that have easily discernible pronuclei and produce large litters for an inbred strain. FVB/N mice are also sensitive to multistage carcinogenesis. See Taketo, M. et al., *P.N.A.S. U.S.A.* 88:2065–2069 (1991), incorporated by reference herein as if set forth in its entirety.

Animals obtained in the method can be screened for integration of the PKCε-encoding polynucleotide and for production of PKCε in the epidermis. A skilled artisan can use known methods to determine whether a transgene has been incorporated into the genome of offspring mice and can readily determine the level of expression of the transgene, for example either by probing for antibodies directed to a tag on the transgene or antibodies directed to the PKCε protein sequence itself. Preferred methods are described in the Example.

Skin tumors can be induced in the mice using a standard initiation-promotion regimen wherein a single dose of a tumor initiator (e.g., DMBA) is applied to the backs of the animals. Several weeks after initiation, a regimen of applying a tumor promoting agent (e.g., TPA) is undertaken. The time required to observe phenotypic changes in treated mice will vary somewhat with the mouse strain and with the level of PKCε expression in the mouse.

The mice of the invention having either squamous cell carcinoma disease or metastatic squamous cell carcinoma disease as described as useful for evaluating the effectiveness of one or more putative agents for treating the disease. For purposes of this invention, an agent is effective if it reduces the incidence or number of carcinomas on an animal or if reduces the severity of the carcinomas or if it reduces or eliminates metastatic disease in those animals in which metastatic disease is observed. In a suitable method for evaluating the effectiveness of a putative agent, the agent, either alone or with a plurality of other putative agents, is administered topically, orally, intraperitoneally, intramuscularly, or in any other suitable manner to an animal or animals having the disease to be treated in an amount to be determined on a case by case basis, but typically on the order of about 1 mg to about 1 gram (preferably in the range of between about 10 mg and about 100 mg) per mouse having a typical weight of about 25 grams. The effect on the animal of the treatment is then evaluated and those agents having an effect on the disease are selected. The agent(s) can have advantageous chemopreventative effect upon the development of metastatic disease in animals of the invention when administered in the same manner to the animal before or after development of squamous cell carcinoma in situ (pre-metastatic carcinoma). One can also screen for agents that reduce or reverse the progression of metastatic squamous cell carcinoma in human and non-human animals using the mice of the invention as a tester.

As a proof of concept, the inventors have demonstrated that when chemopreventative difluoromethylornithine (DFMO) was administered orally in drinking water to mice of the invention at between 50 and 100 mg per mouse, squamous cell carcinomas characteristic of the mice of the invention did not develop after initiation and promotion.

The invention will be better understood upon consideration of the following Example which is to be considered exemplary and not limiting on the scope of the invention

EXAMPLE

Materials and Methods

Materials. TPA and calpain inhibitor I were purchased from Alexis Corporation, San Diego, Calif. DMBA was purchased from Aldrich Chemical Company, Inc., Milwaukee, Wis. Proteasome inhibitor Z-Leu-Leu-Leu-H (aldehyde) (MG132) was purchased from Peptide Institute, Inc., Osaka, Japan. Horseradish peroxidase conjugated anti-T7-Tag antibody was purchased from Novagen, Inc. Madison, Wiss. Rabbit polyclonal antibodies to PKCε and actin were purchased from Santa Cruz Biotechnology, Inc. Santa Cruz, Calif. DAKO immunoperoxidase LSAB®+Kit was purchased from DAKO Corporation, Carpinteria, Calif. Immobilized protein A/G agarose was purchased from Pierce, Rockford, Ill. ECL and ECF Western blotting detection reagents and the protein kinase C enzyme assay system were purchased from Amersham, Arlington Heights, Ill. FVB/NTacfBR mice (FVB/N mice), 7 to 10 weeks of age, were purchased from Taconic Farms, Inc., Germantown, N.Y.

Generation of transgenic lines. Transgenic mice were produced by microinjecting into male pronuclei of one-cell fertilized embryos of FVB/N×FVB/N mice a T7-tagged expression cassette containing an open reading frame encoding PKCε under the control of the human K14 keratinocyte-specific promoter. The K14 promoter has been used successfully to direct overexpression of several different genes to the epidermis, although other keratinocyte-specific promoters such as the K5 promoter can also be used. The protocols for microinjection and for screening for transgenic animals are described in Reddig, P. J. et al., "Transgenic Mice Overexpressing Protein Kinase Cε in Their Epidermis Exhibit Reduced Papilloma Burden but Enhanced Carcinoma Formation after Tumor Promotion," *Cancer Research* 60:595 (2000), already incorporated by reference herein as if set forth in its entirety.

The expression cassette ("transgene") used in the method was produced as follows. The Bgl II/Sal I fragment containing the T7 bacteriophage epitope tag open reading frame from the pET-21c(+) vector (Novagen, Inc.) was ligated to the 5'-terminus of the mouse PKCε cDNA in the pRSV-PKCε vector to produce the pRSV-T7-PKCε vector. The T7-PKCε cDNA from pRSV-T7-PKCε was ligated into the BamH I site of the pGEM3Z-K14 0 β-globin vector by insertion of two Eco47III fragments of the T7-PKCε cDNA, previously linked to Bgl II and BamH I sites, to produce the pGEM3Z-K14-T7-PKCε vector which expressed active T7-PKCε when assayed by immunocomplex kinase assays of CV-1 cells transiently transfected with the T7-PKCε vector (data not shown). The K14-T7-PKCε expression cassette used as the transgene was isolated from pGEM3Z-K14-T7-PKCε by partial digestion with Hind III and complete digestion with endonuclease Ehe I and was purified from the contaminating vector DNA by agarose gel electrophoresis, electroelution, and ion-exchange chromatography. The components of the preferred transgene are presented in the attached Sequence Listing at SEQ ID NOs:1–3 and 5.

Offspring were analyzed for integration of the K1 4-T7-PKCε expression cassette. Genomic DNA obtained from biopsies of tail tissues of weanling mice was digested with EcoRV; the probe was a radiolabelled ~1kb EcoRV/BamH I fragment of pGEM3Z-K14 β-globin vector containing the K14 promoter ligated to the β-globin intron. Nine mice exhibited transgene integration after analysis of 24 potential founder mice. These founder mice were bred to wild-type FVB/N mice to produce F1 offspring. Transgenic F1 mice were bred with other transgenic or wild-type FVB/N mice as necessary to maintain and expand the colony. Mice were housed in groups of 3–4 in plastic-bottom cages in light, humidity, and temperature (24° C.) controlled rooms; food and water were available ad libitum. The animals were kept in a normal rhythm of 12-h light and 12-h dark periods.

F1 mice from each transgene positive line were examined by immunocomplex kinase assay for expression of the transgene. The dorsal skin of the mice was shaved and depilated 24 h before experimentation. The mice were euthanized, the dorsal skin was removed, and the epidermis was scraped off on ice with a razor. The epidermis was placed in 0.5 ml immunoprecipitation (IP) lysis buffer (50 mM HEPES (pH 7.5), 150 mM NaCl, 10% glycerol, 1% Triton X-100, 1.5 mM $MgCl_2$, 10 μg/ml aprotinin, 10 μg/ml leupeptin, 1 mM PMSF, 200 mM $Na_3VO_4$, 200 mM NaF, 1 mM EGTA, 100 mM benzamidine, 5 mg/ml antipain, 5 mg/ml pepstatin, 40 mM MG132, 40 mM calpain inhibitor I), homogenized using a glass Teflon tissue homogenizer, agitated for 30 min at 4° C, centrifuged at 14,000 rpm in a microcentrifuge for 15 min, and the supernatant of the lysate was used for immunoprecipitation. The T7-PKCε transgene product was immunoprecipitated with the anti-T7 antibody. The lysate was pre-absorbed with 5 82 of protein A/G agarose for 10 min at 4° C. Five μg of anti-T7 Tag antibody and 10 μl of protein A/G agarose was added to the lysate and the volume of the lysate was adjusted to 1 ml with lysis buffer. The mixture was incubated for 2–4 h at 4° C. with agitation. The immunoprecipitate was pelleted at 14,000 rpm in a microcentrifuge, washed, and resuspended in 300 ml assay buffer (50 mM Tris (pH 7.4), 5 mM EDTA (pH 8.0), 10 mM EGTA pH 7.9, 0.3% β-mercaptoethanol, 5 μg/ml aprotinin, 5 μg/ml leupeptin, and 50 μg/ml phenylmethylsulfonyl fluoride (PMSF)). The immunoprecipitates were assayed for kinase activity by measuring the incorporation of $^{32}P$ into an epidermal growth factor receptor (EGFR) peptide (ERKRTLRRL; SEQ ID NO:6) in the presence of phosphatidylserine (PS) and TPA. Twenty-five μl of the immunoprecipitate was assayed in kinase buffer containing 0.2 μCi [γ-$^{32}P$ ATP], 50 mM Tris (pH 7.4), 8 mM $MgCl_2$, 0.136 mM ATP, 100 mM EGFR peptide, 3 mM DTT, 34 mg/ml of L-phosphatidyl-L-serine, 3 mg/ml TPA and 1 mM EGTA. The reaction was incubated at 37° C. for 15 min, stopped with 10 ml of 300 mM $H_3PO_4$, spotted onto filter discs, washed with 75 mM $H_3PO_4$, and counted. The assay components are commercially available from Amersham. The amount of activated T7-PKCε kinase activity detected in line 215 was approximately 19-fold greater than that observed in the line 224 mice. Line 206 displayed constitutive T7-PKCε activity, but exhibited no response to the presence of PS and TPA.

Blots probed with the anti-T7 antibody demonstrated that three of these lines were expressing the T7-PKCε transgene. Mouse skin was excised and scraped to remove the subcutaneous tissue. The skin was ground with a mortar and pestle under liquid nitrogen. The ground tissue was homogenized with 5 volumes of PKC extraction buffer (20 mM Tris-HCl (pH 7.4), 0.3% Triton X-100, 2 mM EDTA, 10 mM EGTA, 0.25 M sucrose, 1 mM DTT, 10 μg/ml leupeptin, and 10 μg/ml aprotinin). The homogenate was centrifuged at 100, 000×g for 60 minutes at 4° C. and the supernatant was used as the total PKC extract. Protein concentration in the total PKC extract was determined and 100 μg of total PKC extract protein was fractionated on a 7.5% or 10% SDS-PAGE. The proteins were transferred to 0.45 μm supported nitrocellulose membrane. The membrane was then incubated with anti-T7 Tag (1:2000 dilution) or anti-PKCε (1:100 dilution) antibody, the bound antibody was detected using the appropriate secondary antibodies, and the detection signal was developed with Amersham's ECL or ECF reagents. Immunoblotting of lysates from the immunocomplex kinase assays was also performed with 100 μg of total protein.

Examination of the PKC levels with the anti-PKC antibody demonstrated that the PKC levels were significantly elevated in these transgenic lines. The PKC protein level was the highest in line 215, which positively correlated with the level of PKC activity. The increase in PKC immunoreactive protein levels was 3-, 6-, and 18-fold for line 206, 224, and 215, respectively.

The expression pattern of the T7-PKCε transgene was examined in the skin of transgenic and wild-type mice. Staining with the anti-PKCε antibody was more intense in the dorsal skin of the transgenic mouse than the wild-type littermates. Formalin fixed dorsal skin samples were taken from a wild-type mouse and a line 215 T7-PKCε transgenic mouse. When hybridized with a polyclonal rabbit anti-PKCε antibody, the wild-type dorsal skin sample exhibited light immunoreactivity throughout the epidermis. Light and infrequent nuclear staining was observed. Staining of the hair follicles was also observed in the wild-type dorsal skin. In contrast, PKCε exhibited strong staining in the basal cells of the epidermis and was focally present in the suprabasal layers. An enhancement of PKCε staining in hair follicle epidermal cells was also observed.

Tissue samples from the dorsal and tail base skin from wild-type and transgenic mice were examined histologically. These samples were fixed in formalin, sectioned, and stained with hematoxlin and eosin. All transgenic mice exhibited several phenotypic alterations with line 215 mice exhibiting the greatest penetrance. The mice were phenotypically normal at birth. The phenotypic alterations began around 4 to 5 months of age for the F1 and F2 mice with a mild hyperkeratosis in the tail epidermis (12 out of 26 mice) around 4 months that did not persist. This was accompanied by persistent inflammation at the base of the tail in 26 out of 26 (100%) mice and inflammation of the ears in 20 out of 26 (77%) mice starting about 4 to 5 months of age. The inflammation of the tail base and ears was followed by the formation of ulcerative lesions at these sites around 7–8 months of age in 17 out of 26 (65%) transgenic mice observed. Mild, transient inflammation around the eyes was also observed in 7 out of 26 mice (27%) in line 215 T7-PKCε with a variable age of onset. Although not observed in the F1 mice, ulceration in the proximal dorsal skin that became evident at 5 to 6 months of age occurred in 7 out of 20 (35%) of the F2 mice. Line 224 and 206 exhibited phenotypic abnormalities similar to that observed in line 215 mice. However, the severity of the abnormalities was greatly diminished in those lines.

Histologically, these mice consistently exhibited hyperkeratosis in the dorsal skin, but had no other apparent abnormalities. The grossly affected skin regions displayed several significant alterations. Hyperplasia, characterized by acanthosis, was found in the affected regions along with cellular hypertrophy. Focal regions of necrosis were also evident at sites of ulceration. Mixed inflammatory cell infiltrates were observed in the dermal layer with infiltration into the epidermis and keratinizing layers in affected regions. Prominent amongst the inflammatory cell infiltrates were neutrophils and mast cells.

Tumor Promotion. Mouse skin tumors were induced in the mice (line 215) having an 18-fold higher level of PKCε expression than wild type by the initiation-promotion regimen. At 8–10 weeks of age, the dorsal skins of the mice were shaved 3–4 days before treatment, and those mice in the resting phase of their hair cycle were used for experimentation. The mice were initiated by applying 100 nmol of DMBA in 0.2 ml acetone (or acetone alone as a control) topically to the shaved backs. Two weeks after initiation, 5 nmol of TPA in 0.2 ml acetone (or acetone alone) was applied twice weekly to skin for the duration of the experiment. The number of mice for each experimental group was as follows: DMBA-TPA (wild-type females, 11), (transgenic females, 15), (wild-type males, 20), (transgenic males, 12); DMBA-acetone (wild-type females, 11), (transgenic females, 16), (wild-type males, 19), (transgenic males, 12); Acetone-TPA (wild-type females, 10), (transgenic females, 15), (wild-type males 19), (transgenic males, 11).

At the beginning of the experiment, the eight to ten week old mice exhibited no phenotypic abnormalities. Tumor incidence and burden were observed weekly starting at 4 weeks of TPA promotion. Carcinomas were recorded grossly as downward-invading lesions, a subset of which were examined histologically, and malignancy was confirmed as invading the panniculus carnosus. Carcinoma bearing mice were killed shortly after diagnosis.

Overexpression of PKCε in the epidermis had an unexpected effect on mouse skin tumor promotion by TPA. It had been suggested that PKCε would enhance the effects of tumor promotion. In vitro models of cellular transformation had indicated that PKCε was a potent transforming protein when overexpressed in both fibroblasts and epithelial cells. PKCε alone induced complete transformation of these cells, allowing tumor formation when these cells were injected subcutaneously in athymic mice. However, a dramatic 95% reduction in the papilloma burden was observed when the line 215 transgenic mice were initiated with DMBA and promoted with TPA. Treatment with DMBA and TPA elicited an average of 20 papillomas per mouse in wild-type females and males. In striking contrast, after the same treatment the male and female transgenic mice averaged fewer than 1 papilloma per mouse. For purposes of this invention, an average of fewer than 1 papilloma per mouse is considered to be no papilloma formation. Moreover, the papillomas in the transgenic mice were small, usually less than 2 mm in diameter. Both transgenic and wild-type mice exhibited no differences in weight gain during the course of the experiment. At the end of tumor promotion, the total survival was 92% for the wild-type mice and 88% for the T7-PKCε mice.

In spite of the low papilloma burden, the transgenic mice developed carcinomas independent of papilloma development. After 22 weeks of tumor promotion with DMBA and TPA, 27% of the female and 50% of the male transgenic mice developed carcinomas without prior formation of papillomas. Although wild-type mice treated with DMBA and TPA also developed carcinomas by this time (30% and 15% for females and males, respectively), those carcinomas all developed from existing papillomas. Additionally, 25% of the female transgenic mice treated with DMBA alone developed carcinomas by the twenty-first week of promotion.

At the end of the tumor promotion experiment, the T7-PKCε kinase activity level in papillomas, carcinomas, and uninvolved epidermis on the transgenic mice was measured to determine whether formation of the lesions requires modulation of T7-PKCε kinase activity. The kinase activity level was determined as described above for the T7-PKC immunocomplex kinase assay, but with the following modifications. The skin was not depilated. Skin papillomas and carcinomas were excised before scraping off the uninvolved epidermis. The excised papillomas, carcinomas, and epidermis were separately homogenized and extracted in 0.5 to 1.0 ml of IP lysis buffer. For each treatment group, the epidermis from 3 mice were combined for extraction. Two to four papillomas or 1–2 carcinomas were excised, combined, and extracted in the IP lysis buffer. One hundred mg of the total protein extract, prior to immunoprecipitation, was used for immunoblot analysis.

The levels of precipitable T7-PKCε kinase activity in the epidermal extracts were very similar between each of the treatment groups at 72 and 120 h after the last TPA treatment. The basal (without PS/TPA) and the stimulated (with PS/TPA) T7-PKCε kinase activity levels in extracts from papillomas or carcinomas from DMBA-TPA treated mice were both greatly reduced compared to the levels in the surrounding epidermis. This reduction in kinase activity positively correlated with the reduced level of T7-PKCε protein present in the total, epidermal extracts used for the immunoprecipitations. Thus, it appears that the elevated levels of PKCε activity may inhibit papilloma development and this increased activity may need to be reduced for papillomas to develop. The low levels of immunoreactive PKCε in papillomas from wild-type mice further indicates that a reduction in PKCε levels is important for papilloma formation during tumor promotion.

Also surprisingly, in the absence of prior papilloma growth, the T7-PKCε mice started developing carcinomas between 11 and 12 weeks of tumor promotion in mice treated with DMBA and TPA. The appearance of the T7-PKCε mice resembled mice in a complete carcinogenesis experiment. Additionally, a few of the T7-PKCε mice initiated with DMBA and promoted with acetone developed carcinomas.

The reduction in the T7-PKCε levels in the carcinomas indicates that elevated levels of PKCε are not necessary for the maintenance of the carcinoma. However, the positive correlation between elevated levels of PKCε and carcinoma formation indicates that PKCε can induce the molecular changes necessary for carcinoma formation after treatment of the skin with a single dose of DMBA alone or in conjunction with repeated TPA treatments.

Carcinoma development and metastatic malignant progression of transgenic mice. The T7-PKCε mouse line 215, which expressed T7-PKCε protein approximately 18-fold over endogenous PKCε levels, was further evaluated as above for the development of carcinomas by the DMBA-TPA tumor promotion protocol. At the beginning of the experiment, the 7–9 week old mice exhibited no phenotypic abnormalities. In this experiment, female wild-type and T7-PKCε transgenic mice were treated topically on shaved backs with 100 nmol of DMBA in 0.2 ml acetone. Beginning two weeks later, 0.2 ml acetone or 5 nmol TPA in 0.2 ml acetone was applied twice-weekly to the dorsal skin. The number of mice for each group was as follows: DMBA+ TPA, wild-type mice, 15, T7-PKCε mice, 15; DMBA+ acetone, wild-type mice, 14, T7-PKCε mice, 15.

The tumor incidence and multiplicity were observed weekly starting at 8 weeks of TPA promotion. Carcinomas were recorded by gross observation as downward-invading lesion Carcinoma bearing mice were observed for abnormal tumor growth in the lymph nodes. Wild-type and T7-PKCε mice that were positive for carcinoma formation in the preceding experiment were sacrificed one week after the last treatment with TPA or acetone.

Treatment with TPA for 23 weeks elicited an average of 12 papillomas per wild-type mouse. However, in accordance with the previous findings, the transgenic mice averaged less than 1 papilloma per mouse. The papillomas that developed in transgenic mice were also much smaller than wild-type papillomas.

In spite of the low papilloma burden, the transgenic mice developed carcinoma independently of papilloma development. After 23 weeks of tumor promotion, 6 out of 15 (4%) transgenic mice were evaluated by gross examination as having at least one carcinoma, compared to 1 out of 15 (7%) of the wild-type mice. Wild-type carcinomas developed from existing papillomas. Additionally, 3 out of 15 transgenic mice treated with DMBA+acetone also developed papilloma-independent carcinomas. Wild-type mice treated with DMBA+acetone developed no papillomas.

Because the treatment parameters were identical between this experiment and the prior experiment, the experimental data were normalized and combined to determine whether the development of carcinomas in T7-PKCε after DMBA initiation alone was statistically significant. Using the MSTAT computer program, provided by Dr. Norman Drinkwater (available for free download at http://mcardle.oncology.wisc.edu/Mstat/), initiation by DMBA was shown to be sufficient for squamous cell carcinoma development in the transgenic mice. Two-sided p-values were calculated for tumor and metastasis multiplicity by the Wilcoxon rank sum test. Two-sided p-values were calculated using Fisher's exact test to compare tumor incidence. From the combined data, we determined that DMBA+acetone treatment elicited carcinoma development in 7 out of 31 (22%) T7-PKCε mice, while wild-type mice never developed carcinomas. From the analysis of the combined data, we conclude that DMBA+acetone is sufficient to induce carcinoma development in T7-PKCε mice.

Surprisingly, transgenic mice rapidly developed tumors in regional lymph nodes within three weeks after positive identification of carcinomas by gross observation. Three out of six mice positive for carcinomas also contained regional lymph nodes that bore tumors. The transgenic mice that developed carcinomas with DMBA+acetone treatment did not have evidence of enlarged lymph nodes. However, the positive identification of the carcinomas was less than three weeks before the mice were sacrificed at the conclusion of the experiment.

Tissues to be examined were excised promptly after euthanasia and immediately placed in 10% neutral buffered formalin. Regional lymph nodes with evidence of tumor growth by gross observation were isolated, along with apparently normal lymph node in the same animal. Normal tissue was fixed for 1 hour and carcinomas and lymph nodes were fixed for 2 to 3 hours in the formalin and then embedded in paraffin. 4 mm sections were cut for hematoxylin and eosin staining or immunostaining. Carcinomas were examined by a pathologist. Previous studies demonstrated concordance between gross classification of skin tumors (papilloma vs. carcinoma) and subsequent microscopic evaluation by a pathologist.

By gross observation, both wild-type mouse and T7-PKCε mouse carcinomas were identified by dark red color or the presence of blood clot on the skin surface. As the lesions progressed, necrosis occurred on the surface of the cancer and surface ulceration resulted. Microscopically, cancer cells were identified by the presence of large pleiomorphic nuclei with prominent nucleoli and frequent mitoses. Areas of intracellular keratinization and focal extracellular keratin deposits were identified. The cell cytoplasm was abundant and the cell surface exhibited intercellular bridges. Neutrophils were identified focally adjacent to keratin pearls. The tumors from transgenic mice were moderately differentiated squamous cell carcinoma (MDSC) based on a small number of focal areas with typical squamous epithelium keratin formation, and a large number of areas composed of largely undifferentiated cells. In histological sections of MDSC from two transgenic mice initiated with DMBA and treated for 23 weeks with 5 nmol TPA, malignant cells were seen streaming from the hair follicle, often in the region of the sebaceous gland. This process often involved multiple adjacent hair follicles.

DMBA-initiated mice that had been treated for only 8 weeks with TPA or acetone were also harvested to determine the origin of premalignant lesions. After 8 weeks of TPA treatment, T7-PKCε mice displayed focal areas of increased hair follicle width, epidermal hyperplasia, and hyperkeratosis. Possible premalignant lesions were identified arising from hair follicles; these lesions had cells with enlarged nuclei and prominent nucleoli and showed outward expansion from the hair follicle.

Multiple T7-PKCε transgenic mice exhibited enlarged regional lymph nodes after the identification of primary tumor. The lymphoid tissue, identified by the presence of numerous collections of well-differentiated lymphocytic cells, was infiltrated by squamous cell carcinoma. The carcinoma cells ranged in appearance from undifferentiated clusters of epithelial cells to well differentiated squamous cells producing keratin ("keratin pearls"). Other areas showed undifferentiated carcinoma cells with numerous mitoses identified. The cell morphology was identical to that seen in the primary cancer.

In contrast to T7-PKCε MDSC, the carcinomas of wild-type mice were classified as well differentiated squamous cell carcinoma (WDSC) based on the observation that the majority of the tumor cells had a squamous appearance with abundant keratin formation. Microscopically, extensive areas of intracellular keratinization and focal extracellular keratin deposits were identified. Malignant cells were observed streaming from the epidermis of the papilloma, not from the hair follicle. Epidermal hyperplasia was not observed in the uninvolved skin of wild-type mice.

All mice were harvested one week after the last TPA or acetone treatment; therefore, the common transient effects of TPA treatment on mouse skin, including epidermal hyperplasia and keratinization, should mostly have subsided. This was the case with the uninvolved skin of wild-type mice, which displayed no abnormalities. However, the uninvolved skin of T7-PKCε mice one week after TPA treatment still exhibited hyperplasia of all epidermal cell layers with minimal hyperkeratosis, and small isolated foci of lymphocytic infiltrates were identified within the dermis.

T7-PKCε expressing transgenic mice display almost no papilloma development during treatment with the two-stage DMBA+TPA tumor promotion protocol in comparison to wild-type littermates. However, carcinoma development appears to be enhanced compared to wild-type mice. In an effort to better understand the origin and development of papilloma-independent carcinomas, T7-PKCε mice were further evaluated for the development of carcinomas by the DMBA+TPA tumor promotion protocol.

Histopathological analysis of multiple T7-PKCε mice indicated that squamous cell carcinoma of T7-PKCε mice invaded the dermal region from the hair follicle. The squamous cell carcinoma of T7-PKCε mice rapidly metastasized to regional lymph nodes as soon as 3 weeks after positive identification of carcinoma by gross observation. The tumors from T7-PKCε transgenic mice were classified as moderately differentiated squamous cell carcinoma (MDSC). By comparison, the carcinomas of wild-type mice, which appeared to originate from the interfollicular epidermis of papillomas, were classified as well differentiated squamous cell carcinoma (WDSC). WDSC derived from papillomas invaded the dermal area with no evidence of metastatic progression.

The present invention is not intended to be limited to the foregoing, but to include all such variations and modifications as come within the scope of the appended claims.

We claim:

1. A genetically modified FVB/N mouse having epidermal cells that comprise a protein kinase Cε activity higher than that of wild-type FVB/N epidermal cells.

2. An FVB/N mouse as claimed in claim 1 wherein the protein kinase Cε level is at least 5-fold higher than that of wild-type FVB/N epidermal cells.

3. An FVB/N mouse as claimed in claim 1 wherein the protein kinase Cε level is at least 12-fold higher than that of wild-type FVB/N epidermal cells.

4. An FVB/N mouse as claimed in claim 1 wherein the protein kinase Cε level is at least 15-fold higher than that of wild-type FVB/N epidermal cells.

5. An FVB/N mouse as claimed in claim 1 wherein the protein kinase Cε level is at least 18-fold higher than that of wild-type FVB/N epidermal cells.

6. An FVB/N mouse as claimed in claim 1 wherein the mouse exhibits metastatic squamous cell carcinoma disease.

7. An FVB/N mouse as claimed in claim 1 comprising in the epidermal cells a transgene that comprises a polynucleotide that encodes Protein Kinase Cε under the transcriptional control of an upstream promoter active in keratinocytes and a downstream polyA addition sequence.

8. An FVB/N mouse as claimed in claim 7 wherein the upstream promoter is a keratin promoter.

9. An FVB/N mouse as claimed in claim 8 wherein the upstream promoter is a K14 promoter.

10. An FVB/N mouse as claimed in claim 7 further comprising a transcription enhancing element.

11. An FVB/N mouse as claimed in claim 10 wherein the transcription enhancing element is a β-globin intron sequence.

12. An FVB/N mouse as claimed in claim 7 wherein the transgene comprises SEQ ID NO:3.

13. A transgenic mouse whose somatic and germ cells contain a chimeric DNA sequence comprising a keratin promoter/regulatory sequence operably linked to a sequence encoding protein kinase Cε, wherein epidermal expression of said protein kinase Cε results in a phenotype selected from the group consisting of inflammation, hyperkeratosis, hyperplasia, cellular hypertrophy, and ulceration.

14. An FVB/N mouse as claimed in claim 1 wherein the mouse is suppressed for papilloma production and susceptible to developing squamous cell carcinoma after tumor in initiation and promotion.

15. An FVB/N mouse as claimed in claim 14 wherein the mouse is further susceptible to developing metastatic squamous cell carcinoma after tumor initiation and promotion.

16. A method for inducing squamous cell carcinoma in an FVB/N mouse suppressed for formation of papillomas, the method comprising the steps of:

treating an FVB/N mouse having epidermal cells that comprise a protein kinase C$\epsilon$ activity higher than that of wild-type FVB/N epidermal cells with a tumor initiating agent; and treating the initiated mouse repeatedly with a tumor promoting agent until the mouse develops squamous cell carcinoma while suppressing formation of papillomas.

17. A method as claimed in claim 16 wherein the tumor initiating agent is 7,12-dimethylbenz[a]anthracene and the tumor promoting agent is 12-O-tetradecanoylphorbol-13-acetate.

18. A method as claimed in claim 16 wherein the protein kinase C$\epsilon$ activity is at least 12-fold higher than that of wild-type FVB/N epidermal cells and wherein the squamous cell carcinoma is metastatic.

19. A method as claimed in claim 18 wherein the protein kinase C$\epsilon$ activity is at least 15-fold higher than that of wild-type FVB/N epidermal cells.

20. A method as claimed in claim 18 wherein the protein kinase C$\epsilon$ activity is at least 18-fold higher than that of wild-type FVB/N epidermal cells.

21. A method as claimed in claim 16 wherein the epidermal cells of the FVB/N mouse comprise a polynucleotide that encodes Protein Kinase C$\epsilon$ under the transcriptional control of an upstream promoter active in keratinocytes and a downstream polyA addition sequence.

22. A method for evaluating effectiveness of a putative agent as a chemopreventative against squamous cell carcinoma disease in a mammal, the method comprising the steps of:

administering at least one putative agent to papilloma-suppressed FVB/N mice having epidermal cells that comprise a protein kinase C$\epsilon$ activity higher than that of wild-type FVB/N epidermal cells, wherein the mice are susceptible to squamous cell carcinoma disease after tumor initiation and promotion, and wherein the agent is administered in an amount effective to prevent onset of the disease;

treating the mice with a tumor initiating agent; and treating the initiated mice repeatedly with a tumor promoting agent evaluating the effectiveness of the at least one putative agent; and selecting from the at least one putative agent an effective chemopreventative agent.

* * * * *